(12) United States Patent
Verboom

(10) Patent No.: US 8,529,878 B2
(45) Date of Patent: Sep. 10, 2013

(54) METHOD FOR STRENGTHENING KERATINOUS FIBERS

(75) Inventor: Gilles M. Verboom, St. Charles, IL (US)

(73) Assignee: Alberto Culver Company, Englewood Cliffs, NJ (US)

( * ) Notice: Subject to any disclaimer, the term of this patent is extended or adjusted under 35 U.S.C. 154(b) by 217 days.

(21) Appl. No.: 13/061,823

(22) PCT Filed: Sep. 3, 2009

(86) PCT No.: PCT/US2009/055895
§ 371 (c)(1), (2), (4) Date: Apr. 15, 2011

(87) PCT Pub. No.: WO2010/028153
PCT Pub. Date: Mar. 11, 2010

(65) Prior Publication Data
US 2011/0186070 A1 Aug. 4, 2011

Related U.S. Application Data

(60) Provisional application No. 61/093,992, filed on Sep. 3, 2008.

(51) Int. Cl.
*A61Q 5/00* (2006.01)

(52) U.S. Cl.
USPC .................................................. 424/70.122

(58) Field of Classification Search
None
See application file for complete search history.

(56) References Cited

U.S. PATENT DOCUMENTS

| | | | |
|---|---|---|---|
| 4,421,602 A | 12/1983 | Brunnmueller et al. | |
| 4,713,236 A | 12/1987 | Hoover et al. | |
| 4,992,267 A | 2/1991 | DenBeste et al. | |
| 5,478,553 A | 12/1995 | Chandran et al. | |
| 5,632,977 A | 5/1997 | Chandran et al. | |
| 5,989,534 A | 11/1999 | Samain | |
| 6,231,876 B1 | 5/2001 | Niessner et al. | |
| 6,271,327 B1 | 8/2001 | Niessner et al. | |
| 6,471,953 B1 | 10/2002 | N'Guyen et al. | |
| 6,589,510 B2 | 7/2003 | Kalbfleisch et al. | |
| 6,800,302 B2 | 10/2004 | Cannell et al. | |
| 2003/0199642 A1 | 10/2003 | Schneider et al. | |
| 2006/0260632 A1 | 11/2006 | Campain | |
| 2006/0286057 A1 | 12/2006 | Cannell et al. | |
| 2007/0110690 A1 | 5/2007 | Nguyen et al. | |
| 2008/0182773 A1 | 7/2008 | Gauweiler et al. | |
| 2008/0260666 A1* | 10/2008 | Giroud et al. | 424/62 |
| 2008/0274070 A1 | 11/2008 | Campain et al. | |
| 2009/0202465 A1 | 8/2009 | Mougin et al. | |
| 2009/0269295 A1 | 10/2009 | Benabdillah et al. | |
| 2011/0048447 A1 | 3/2011 | Muller et al. | |
| 2011/0180092 A1 | 7/2011 | Verboom et al. | |
| 2011/0180093 A1 | 7/2011 | Verboom et al. | |
| 2011/0186070 A1 | 8/2011 | Verboom | |
| 2011/0192414 A1 | 8/2011 | Verboom et al. | |
| 2011/0192415 A1 | 8/2011 | Verboom et al. | |

FOREIGN PATENT DOCUMENTS

| | | |
|---|---|---|
| EP | 0 190 834 A2 | 8/1986 |
| EP | 0 524 346 A1 | 1/1993 |
| EP | 1 779 894 A1 | 5/2007 |
| EP | 1 977 731 A1 | 10/2008 |
| EP | 1 977 732 A1 | 10/2008 |
| EP | 2 149 363 A2 | 2/2010 |
| FR | 2887887 A1 | 1/2007 |
| FR | 2910274 A1 | 6/2008 |
| JP | 2002-255756 A | 9/2002 |
| WO | WO 89/04653 A1 | 6/1989 |
| WO | WO 02/15854 A1 | 2/2002 |
| WO | WO 2005/020943 A1 | 3/2005 |
| WO | WO 2007/003784 A1 | 1/2007 |
| WO | WO 2007/135299 A1 | 11/2007 |
| WO | WO 2009/079288 A1 | 6/2009 |
| WO | WO 2010/028137 A2 | 3/2010 |
| WO | WO 2010/028142 A2 | 3/2010 |
| WO | WO 2010/028143 A2 | 3/2010 |
| WO | WO 2010/028147 A2 | 3/2010 |
| WO | WO 2010/028153 A2 | 3/2010 |

OTHER PUBLICATIONS

"Heat Protection for Hair Care" Dow Corning, http://web.archive.org/web/20040630102903/http://www.dowcorning.com/content/Publishedlit/HEATPROTECT.pdf (2004).
"Lupamin 9095 High Molecular Weight Liner Polyvinylamine," basf, http://www2.basf.us/businesses/chemicals/performance/pdfs/Lupamin_9095.pdf, retrieved Jun. 15, 2011.
Syed et al., "Water-Soluble Polymers in Hair Care, Prevention and Repair of Damage during Hair Relaxing," *Water Soluble Polymers: Solution Properties and Applications*, Symposium, pp. 231-244 (Sep. 1997).
European Patent Office, International Search Report in International Application No. PCT/US2009/055895 (Jul. 4, 2011).
European Patent Office, International Preliminary Report on Patentability in International Application No. PCT/US2009/055895 (Jul. 28, 2011).
European Patent Office, International Search Report in International Application No. PCT/US2009/055880 (Jul. 15, 2011).
European Patent Office, International Preliminary Report on Patentability in International Application No. PCT/US2009/055880 (Jul. 28, 2011).
European Patent Office, International Search Report in International Application No. PCT/US2009/055886 (Sep. 23, 2011).

(Continued)

*Primary Examiner* — Jyothsna Venkat
(74) *Attorney, Agent, or Firm* — Ronald A. Koatz

(57) ABSTRACT

Provided is method of strengthening keratinous fibers that includes contacting the fibers with a composition that includes a poly(vinylamine-vinylformamide) copolymer and a carrier, wherein the treated fibers exhibit an improvement in strength. Also provided are methods for improving strength of fibers that have been damaged, e.g., as a result of having been subjected to chemical and/or thermal treatment processes that diminish fiber strength, by contacting the fibers with the composition.

8 Claims, No Drawings

(56) References Cited

OTHER PUBLICATIONS

European Patent Office, International Preliminary Report on Patentability in International Application No. PCT/US2009/055886 (Oct. 13, 2011).

European Patent Office, International Search Report in International Application No. PCT/US2009/055882 (Sep. 23, 2011).

European Patent Office, International Preliminary Report on Patentability in International Application No. PCT/US2009/055882 (Oct. 13, 2011).

European Patent Office, International Search Report in International Application No. PCT/US2009/055873 (Sep. 30, 2011).

European Patent Office, International Preliminary Report on Patentability in International Application No. PCT/US2009/055873 (Sep. 30, 2011).

* cited by examiner

METHOD FOR STRENGTHENING KERATINOUS FIBERS

BACKGROUND OF THE INVENTION

Hair styling or hair setting compositions are widely used by consumers in the cosmetic industry to retain a particular shape or style of the hair. Hair styling compositions can assist in manipulating or styling the hair, providing temporary benefits in holding the shape of the hairstyle (fixing) and/or maintaining the shine or appearance (grooming, restyling) of the hair, e.g., in the evening, during the day, between hair washing periods, or between subsequent hair setting procedures.

Hair styling compositions also can be subjectively evaluated, e.g., by visual and tactile sensory methods (e.g., by visual examination and touching) for characteristics such as appearance (shine, cleanliness, naturalness of appearance and texture), feel (stiffness, tackiness, softness), curl memory (bounce, and restylability), ease of combing and brushing the hair, residue (flaking), static, smoothness, and the like. Also of importance are the aesthetic characteristics and appearance provided by hair styling compositions before, during, and after application to hair. Preferably, the product viscosity should be non-runny to avoid dripping during application. The product should be easy to spread, have a smooth texture, a non-tacky feel, and be able to dry relatively quickly on the hair.

However, hair is often subjected to a wide variety of stresses and treatments that can cause damage to the hair. These include shampooing, rinsing, drying, heating, combing, styling (such as relaxing or straightening), penning, bleaching, coloring, exposure to the elements, thermo processes, and the like. Such stresses can leave the hair in a dry, rough, lusterless, or frizzy condition, which can be caused, e.g., by repeated abrasion of the hair surface and removal of the hair's natural oils and other natural conditioning and moisturizing components. Additionally, hair is often subjected to weather-related stresses, e.g., sunlight, wind, and changes in temperature and humidity, which can cause hair damaged and other conditions considered by consumers to be cosmetically undesirable. Such stresses are detrimental to the hair fiber, and often result in decreased hair fiber strength.

Hair-setting compositions that include one or more hair-setting polymers to impart styling and/or fixative properties have been disclosed. For example, U.S. Pat. No. 4,713,236 describes compositions that include amine-containing polymers and copolymers that contain a primary pendant amine group, for imparting conditioning properties to hair. U.S. Pat. Nos. 5,478,553 and 5,632,977 describe hair fixative compositions containing polymeric n-vinyl formamide and methods of treating hair. U.S. Published Patent Application No. 2007/0110690 describes a process for inhibiting hair from becoming frizzy that involves contacting hair with anionic silicone and with polyvinylamine. However, such conventional hair styling methods do not necessarily promote hair fiber strength, particularly in hair that has been damage as a result of exposure to the stresses discussed above.

Accordingly, there is a need for methods of hair styling that serve to increase hair strength, preferably while maintaining desirable subjective properties, e.g., smooth texture, curl memory, bounce, naturalness of appearance, etc. The present invention provides such methods.

BRIEF SUMMARY OF THE INVENTION

The present invention provides a method for strengthening keratinous fibers, such as mammalian hair, which includes contacting the fibers with a strengthening-effective amount of a composition that includes a poly(vinylamine-vinylformamide) copolymer and a carrier, and optionally styling the hair treated with the composition.

The invention further provides a method of strengthening damaged or weakened keratinous fibers, which includes contacting the damaged or weakened fibers with a strengthening-effective amount of a composition comprising a poly(vinylamine-vinylformamide) copolymer and a carrier and optionally styling the treated fibers. The fibers can include fibers damaged or weakened as a result, e.g., of chemical contact, mechanical stress, heat, or a combination thereof. Such damage can occur when keratinous fibers are subjected to one or more treatments such as, e.g., bleaching, coloring, penning, relaxing, straightening, combing, brushing, toweling, or a combination thereof.

DETAILED DESCRIPTION OF THE INVENTION

In accordance with the present invention, keratinous fibers such as, e.g., mammalian (e.g., human) hair, are treated with a composition that includes one or more poly(vinylamine-vinylformamide) copolymers in an amount effective to promote increased strength of the hair fiber. The method of the present invention is believed to be particularly useful for increasing the strength of hair fibers that have been damaged or weakened as a result, e.g., of chemical contact, mechanical stress, heat, or a combination thereof. Such damage can occur when hair is subjected to one or more treatments such as, e.g., bleaching, coloring, perming, relaxing, straightening, combing, brushing, toweling, or a combination thereof, which decrease hair fiber strength and weaken the hair. The method of the present invention preferably increases hair strength by at least about 5% using an F20 fatigue index obtained in tensile strength testing, and more preferably by at least about 10%. The hair can be contacted with the composition for any effective amount of time, e.g. from about 1 minute to about 30 minutes, from about 1 minutes to about 20 minutes, or from about 5 minutes to about 10 minutes. Deposition of the copolymers onto hair fibers can be suitably measured using load cells to monitor weight before, during and/or after treatment with the composition.

The composition used in accordance with the method of the present invention preferably includes one or more poly (vinylamine-vinylformamide) copolymers as a styling polymer. In some embodiments, the composition used in accordance with the method of the present invention can include one or more linear poly(vinylamine-vinylformamide) copolymers, a polyvinylpyrrolidone polymer and an aqueous carrier. The poly(vinylamine-vinylformamide) copolymer is preferably present in the composition in a hair-styling effective amount, e.g., in an amount effective to promote at least about 50% curl retention in the hair after about 2 hours under conditions of about 90% relative humidity and a temperature about 75° F., when the composition is applied to mammalian hair. Suitable poly(vinylamine-vinylformamide) copolymers can be obtained, e.g., by partial hydrolysis of a polyvinylformamide, to produce one or more copolymers that contain vinylamine and vinylformamide monomeric units. Poly(vinylamine-vinylformamide) copolymers, which can be used as a styling polymer in the composition of the present invention, include the polymers contained in products sold under the trademark LUPAMIN®, which are sold by BASF and are supplied as aqueous solutions containing linear poly(vinylamine-vinylformamide) copolymers. The polymers in LUPAMIN® are prepared by polymerization of vinylformamide followed by partial hydrolysis of the polyvinylformamide. Exemplary poly(vinylamine-vinylformamide) copolymers, which can be used in the composition, include the polymers contained in LUPAMIN® 9095, LUPAMIN® 9050, LUPAMIN® 9030, LUPAMIN® 9010, LUPAMIN® 5095 and LUPAMIN® 1595.

The digits used in conjunction with the LUPAMIN® product name correspond to the molecular weight and the extent of hydrolysis of the polymer. The first two (i.e., first and second) digits in the product name correspond to the polymer molecular weight. For instance, the first two digits in LUPAMIN® 9095, LUPAMIN® 9050, LUPAMIN® 9030 and LUPAMIN® 9010, i.e., "90," are indicative of the polymer molecular weight polymer. The average molecular weights of exemplary polymers and other properties associated with corresponding LUPAMIN® products, as published in BASF's technical bulletins, are summarized below in Table A.

TABLE A

|  | Lupamin ® 9095 | Lupamin ® 9030 | Lupamin ® 9010 | Lupamin ® 5095 | Lupamin ® 1595 |
|---|---|---|---|---|---|
| Form | Liquid | Liquid | Liquid | Clear Pale Yellow Liquid | Clear Pale Yellow Liquid |
| Density (g/mL) | 1.08 | 1.08 | 1.08 | 1.08 | 1.08 |
| % Solids (wt %) | 20-22% | 16-18% | 13-15% | 21-24% | 28-32% |
| % Polymer (wt %) | 6-8 | 10-12 | 12-14* | 8-12 | 9-11 |
| Ave. Molecular Weight (g/mol) | 340,000 | 340,000 | 340,000 | 45,000 | <10,000 |
| Viscosity (mPas at 20° C.) | >5000 | <5000 | <5000 | <1000 | <1000 |
| pH | 7-9 | 7-9 | 7-9 | 7-9 | 7-9 |

*estimated based on solids content, hydrolysis index and polymer content relative to total solids reported for other LUPAMIN ® products
LUPAMIN ® 9050 is believed to have a molecular weight of 340,000 based on the molecular weights reported in BASF's technical bulletins for LUPAMIN ® 9095, 9030 and 9010.
LUPAMIN ® 9050 is believed to have a solids content of about 16-19 wt % based on the results of solids testing performed on a product sample and solids content reported for LUPAMIN ® 9095, 9030 and 9010.
LUPAMIN ® 9050 is estimated to have a poly(vinylamine-vinylformamide) copolymer content (i.e., polymer content) of about 9-12 wt % based on solids testing, and reported solids and polymer content for other LUPAMIN ® products.

The last two (i.e., third and fourth) digits used in conjunction with the LUPAMIN® product name represent the "hydrolysis index," which corresponds to the percent of the formamide functional groups in the polymer that have been hydrolyzed and converted into vinylamine units. For instance, the last two digits in LUPAMIN® 9095, i.e., "95," indicate the degree of hydrolysis, i.e., that the polymer is about 95% hydrolyzed (or greater than 90% hydrolyzed as noted in BASF's technical bulletins for Lupamin° 5095 and Lupamin° 1595). Thus, the polymers contained in LUPAMIN® 9095, LUPAMIN® 5095 and LUPAMIN® 1595 are believed to contain about 95% vinylamine monomeric units (vinylamine monomers) and about 5% vinylformamide monomeric units (vinylformamide monomers). By contrast, LUPAMIN® 9050 is believed to contain about 50% vinylamine monomers and about 50% vinylformamide monomers, LUPAMIN® 9030 is believed to contain about 30% vinylamine monomers and about 70% vinylformamide monomers, and LUPAMIN® 9010 is believed to contain about 10% vinylamine monomers and about 90% vinylformamide monomers.

The composition used in accordance with the method of the present invention also can include two or more poly(vinylamine-vinylformamide) copolymers. In some embodiments, combinations of two or more poly(vinylamine-vinylformamide) copolymers may be found to promote unexpectedly superior hair strength properties. In one embodiment, the composition used in accordance with the method of the present invention includes at least one high molecular weight poly(vinylamine-vinylformamide) copolymer and at least one low molecular weight poly(vinylamine-vinylformamide) copolymer. As used herein, a high molecular weight poly(vinylamine-vinylformamide) copolymer refers to a poly(vinylamine-vinylformamide) copolymer with an average molecular weight greater than about 100,000 g/mole and a low molecular weight poly(vinylamine-vinylformamide) copolymer refers to a poly(vinylamine-vinylformamide) copolymer with an average molecular weight of about 100,000 g/mole or less.

The high molecular weight poly(vinylamine-vinylformamide) copolymer can include, e.g., at most about 95% vinylamine monomers (e.g., about 95% vinylamine monomers and about 5% vinylformamide monomers), at most about 50% vinylamine monomers (e.g., about 50% vinylamine monomers and about 50% vinylformamide monomers), at most about 30% vinylamine monomers (e.g., about 30% vinylamine monomers and about 70% vinylformamide monomers), or at most about 10% vinylamine monomers (e.g., about 10% vinylamine monomers and about 90% vinylformamide monomers). Suitable high molecular weight poly(vinylamine-vinylformamide) copolymers include, for example, LUPAMIN® 9095, LUPAMIN® 9050, LUPAMIN® 9030 and LUPAMIN® 9010 polymers. The low molecular weight poly(vinylamine-vinylformamide) copolymer can include, e.g., at most about 95% vinylamine monomers (e.g., about 95% vinylamine monomers and about 5% vinylformamide monomers). Suitable low molecular weight poly(vinylamine-vinylformamide) copolymers include, e.g., LUPAMIN® 5095 and LUPAMIN® 1595 polymers.

The poly(vinylamine-vinylformamide) copolymer can be present in the composition, e.g., in an amount of from about 0.01 wt % to about 100 wt %, from about 0.1 wt % to about 50 wt %, from about 2 wt % to about 50 wt %, from about 1 wt % to about 30 wt %, from about 2 wt % to about 30 wt %, or from about 5 wt % to about 30 wt %. In some embodiments, the poly(vinylamine-vinylformamide) copolymer can be present in the composition, e.g., in an amount of from about 0.01 wt % to about 10 wt %, from about 0.05 wt % to about 10 wt %, from about 0.1 wt % to about 10 wt %, from about 0.1 wt % to about 10 wt %, from about 0.1 wt % to about 5 wt %, or from about 0.1 wt % to about 2 wt %.

The composition used in accordance with the method of the present invention can include polyvinylpyrrolidone (PVP), which has been found to provide the hair with good styling performance and desirable subjective properties such as, e.g., gloss, low flaking and smooth texture, without sacrificing hair strength. The composition can thus include polyvinylpyrrolidone, e.g., in an amount of from about 0.01 wt % to about 20 wt %, from about 0.05 wt % to about 15 wt % polyvinylpyrrolidone, from about 0.1 wt % to about 10 wt % polyvinylpyrrolidone, from about 0.1 wt % to about 5 wt % polyvinylpyrrolidone, from about 0.1 wt % to about 1 wt % polyvinylpyrrolidone, or from about 0.5 wt % to about 1 wt % polyvinylpyrrolidone.

The composition used in accordance with the method of the present invention can further include one or more additional ingredients such as, for example, a conditioning agent, a film former or modifier (in addition to PVP), a thickener, a surfactant, an emollient, an emulsifier, a propellant, a fatty alcohol, and the like, and combinations thereof. The composition preferably exists in the form of a mousse or a gel.

Suitable additional film formers beyond PVP can include, e.g., vinylpyrrolidone copolymers, cationic cellulose derivatives, polyurethanes, acrylates/hydroxyester acrylate copolymer, celluloses and polysaccharide gums and their derivatives and the like, and combinations thereof. The composition used in accordance with the method of the present invention can include, for example, from about 0.01 wt % to about 10 wt % of one or more additional film formers, from about 0.05 wt % to about 5 wt % of one or more additional film formers, or from about 0.1 wt % to about 5 wt % of one or more additional film formers. Suitable film forming polymers also can include, e.g., one or more nonionic copolymers of N-vinylpyrrolidone, methacrylamide and N-vinylimidazole.

Suitable film forming polymers also can include, e.g., one or more copolymers of vinylpyrrolidone and dimethylaminoethyl methacrylate(s). The composition of the present invention can include, e.g., from about 0.01 wt % to about 15 wt % of one or more film forming vinylpyrrolidone copolymers, e.g., from about 0.05 wt % to about 10 wt % of one or more film forming vinylpyrrolidone copolymers, or from about 0.1 wt % to about 10 wt % of one or more film forming vinylpyrrolidone copolymers. Exemplary film forming vinylpyrrolidone copolymers include LUVISET® CLEAR, available from BASF, and VP/dimethylaminoethyl methacrylate copolymer 845-G.

Suitable film formers further can include, e.g., cationic cellulose derivatives. The composition can include, for example, from about 0.01 wt % to about 10 wt % of one or more cationic cellulose derivatives, from about 0.02 wt % to about 5 wt % of one or more cationic cellulose derivatives, or from about 0.05 wt % to about 5 wt % of one or more cationic cellulose derivatives. A preferred class of cationic cellulose derivatives include copolymers of a hydroxyethylcellulose and diallyldimethyl ammonium chloride. An exemplary cationic cellulose derivative is polyquaternium-4, a copolymer of cellulose, 2-hydroxyethyl ether and diallyldimethyl ammonium chloride. Polyquaternium-4 is the active ingredient in products marketed under the names CELQUAT® H-100 and CELQUAT® L-200. It will be appreciated that some film formers, e.g., CELQUAT® H-100 also may function as conditioning agents.

Suitable film modifiers can include, for example, one or more aminosilicones, one or more PEG-n dimethicones, one or more PEG-n/PPG-n dimethicones, one or more cyclomethicones, one or more plasticizers (e.g., glycols, glycol ethers, glycerine), and the like, and combinations thereof. Suitable dimethicones can include polyethylene/propylene glycol derivatives of dimethicone containing an average of n moles of ethylene/propylene oxide, e.g., where n is in the range of about 3 to about 20. An exemplary PEG-n/PPG-n dimethicone includes a PEG-18/PPG-18 dimethicone, available from Dow Corning under the trade name DC-190. The composition used in accordance with the method of the present invention can include, e.g., from about 0.01 wt % to about 10 wt % of one or more film modifiers, from about 0.02 wt % to about 5 wt % of one or more film modifiers, or from about 0.05 wt % to about 5 wt % of one or more film modifiers.

Suitable thickeners can include, e.g., one or more associative and non-associative thickeners, one or more polysaccharides, polysaccharide derivatives, gums (e.g., guar gum, xanthan gum), and the like, and combinations thereof. Suitable associative thickeners can include, e.g., acrylates/beheneth-25 acrylate copolymers, polyether-1/1,3-butylene glycol blends, and combinations thereof. The composition used in accordance with the method of of the present invention can include, for example, from about 0.01 wt % to about 15 wt % of one or more thickeners, from about 0.05 wt % to about 8.0 wt % of one or more thickeners, or from about 0.1 wt % to about 3.0 wt % of one or more thickeners. Exemplary thickeners include TINOVIS® GTC, available from Ciba Specialty Chemicals, PURE THIX® HH, available from Southern Clay, and combinations thereof.

Suitable fatty alcohols in the composition used in accordance with the method of the present invention can include linear or branched, saturated or unsaturated $C_8$-$C_{24}$ fatty alcohol. The fatty alcohols can be selected from the group consisting of myristyl alcohol, cetyl alcohol, stearyl alcohol, oleyl alcohol, behenyl alcohol, or the like, and mixtures thereof. The fatty alcohols can be present in any suitable amount.

Suitable emulsifiers in the composition used in accordance with the method of the present invention can include stearamidopropyl dimethylamine, glyceryl esters, particularly those with an HLB value of about 3 to about 4, for example, about 3.5 to about 4.0 (such as glyceryl stearate), or the like, and mixtures thereof. The emulsifier can be present in any suitable amount.

The aqueous carrier can include any suitable quantity of water, e.g., from about 25 wt % to about 97 wt % water (e.g., from about 30% to about 95% water). Preferably, the composition includes from about 50 wt % to about 97 wt %, and more preferably from about 70 wt % to about 90 wt %, and most preferably from about 80 wt % to about 90 wt % water. Preferably, the water used in the composition is deionized water.

Suitable conditioning agents can include, for example, one or more amphoteric copolymers, one or more amphoteric terpolymers, one or more cationic conditioners and the like, and combinations thereof. Suitable conditioning agents can include amphoteric terpolymers of acrylic acid, diallyl dimethyl ammonium chloride, and acrylamide. The composition used in accordance with the method of the present invention can include, for example, from about 0.01 wt % to about 20 wt % of one or more conditioning agents, from about 0.01 wt % to about 15 wt % of one or more conditioning agents, or from about 0.05 wt % to about 10 wt % of one or more conditioning agents. An exemplary conditioning agent is polyquaternium-39, sold under the tradename MERQUAT® PLUS 3330, available from Nalco Co. Other exemplary products that may serve as conditioning agents include polyquaternium-4 and/or VP/dimethylaminoethyl methacrylate copolymer 845-G.

Suitable surfactants can include, e.g., one or more anionic, nonionic, cationic, and amphoteric surfactants, with nonionic, cationic, and amphoteric surfactants being preferred. Exemplary surfactants include PPG-5/Ceteth 20, Oleth-20, polysorbate-20, and cocamidopropyl betaine. The composition used in accordance with the method of the present invention can include, for example, from about 0.01 wt % to about 20 wt % of one or more surfactants, from about 0.01 wt % to about 15 wt % of one or more surfactants, or from about 0.05 wt % to about 10 wt % of one or more surfactants.

The hair styling composition used accordance with the method of in the present invention can include other components that may be suitable for use in conventional hair styling compositions such as, e.g., conventional hair fixative, hair setting and/or hair grooming gels, rinses, emulsions (oil-in-water, water-in-oil or multiphase), lotions, creams, pomades, sprays (pressurized or non-pressurized), spritzes, mousses, foams, shampoos, conditioners, and solids (e.g., as sticks, semisolids and the like). Additional cationic polymers or anionic polymers can be used in accordance with the invention to further increase strength and/or promote other desirable properties with respect to the keratinous fibers such as, e.g., shine and/or appearance.

If desired, the composition used in accordance with the method of the present invention can include a propellant, e.g., for dispensing the composition (e.g., in the form of a mousse or gel). The composition can include, for example, from about 0.01 wt % to about 20 wt % of one or more propellants, from about 0.01 wt % to about 15 wt % of one or more propellants, or from about 0.05 wt % to about 10 wt % of one or more propellants. Exemplary propellants include propane, butane, and mixtures thereof.

In accordance with the method of the present invention, the keratinous fibers may be optionally styled in any suitable manner. In addition, the composition can be applied in any suitable manner, e.g., by working the composition through the hair, e.g., with the hands and fingers or with a suitable implement such as, e.g., a comb or brush, to ensure uniform coverage.

The present invention further provides a method of strengthening damaged keratinous fibers, which includes contacting the damaged fibers with a strengthening-effective amount of a composition comprising a poly(vinylamine-vinylformamide) copolymer and an aqueous carrier and optionally styling the damaged fibers. The damaged fibers can include fibers damaged by at least one potentially hair-damaging treatment such as, e.g., one or more treatments that include chemical and/or heat application, e.g., bleaching, coloring, perming, relaxing, straightening, and the like.

The increase in hair fiber strength is preferably measured with an F20 Index. The F20 Index is commonly used as a method to determine if hair fibers have been altered by treatment with cosmetic products. The F20 Index is determined by extending the fibers to 20% of their length before and after treatment of the fibers. In this test, a dry single fiber is stretched to 20% strain or elongation at a specified constant rate (elongation per minute). The area under the curve (Energy) required to stretch the fiber to 20% strain is used to assess the condition of the fiber. The index values (After/Before Treatment) are calculated and used to assess the extent of hair damage. An Index of less than 1.0 indicates damage to the hair fiber produced by the chemical hair product. A percentage may be used to express the changes in the stress for a fixed strain of fibers. Moreover, as part of measuring the F20 Index as part of tensile strength determination, a profile can be taken of the hair fibers tested which also includes a plateau load and a break load of the fiber.

In some embodiments, the method of the present invention results in fibers with increased strength that exhibit at least about 1.05 F20 Index. In other embodiments, the method of the present invention results in fibers with increased strength that exhibit at least about 1.1 F20 Index. Accordingly, the method of the present invention preferably increases hair strength by at least about 5% using an F20 fatigue index obtained in tensile strength testing, and more preferably by at least about 10%.

The following examples further illustrate the invention but, of course, should not be construed as in any way limiting its scope.

EXAMPLE 1

This example demonstrates a method for increasing hair fiber strength. Start with dry tresses, such as are available from International Hair Importers in 8 inch [20.3 cm] lengths cut in 1 inch [2.5 cm] wide swatches. Pre-cleanse tresses with warm tap water at approximately 35-40° C. flowing at about 2 gallons/minute [7570 cc/minute]. Rinse for about 30 seconds and then squeeze out excess water and towel dry with cleaning tissues such as KIMWIPES™.

Apply to tresses a strengthening-effective amount of a composition comprising a poly(vinylamine-vinylformamide) copolymer, e.g., LUPAMIN® 9095, and an aqueous carrier. Massage in with fingers and then comb through twice with large teeth and then twice with small teeth of a two-sided comb. Leave in for about 10 minutes and then squeegee out excess solution. Allow the tress to stand for a fixed period of time and then determine tensile strength by testing tress profiles for treated and untreated hair sufficient to measure the F20 Index, while also testing plateau load and break load of the fibers.

It is believed that the composition applied to the tresses will result in improved hair strength by increasing the F20 Index and by increasing the plateau load and break load of the treated fibers.

EXAMPLE 2

This example demonstrates a method for increasing fiber strength in damaged hair. Start with bleached and/or mechanically damaged tresses, such as are commercially available from International Hair Importers in 8 inch [20.3 cm] lengths cut in 1 inch [2.5 cm] wide swatches. Pre-cleanse the damaged tresses with warm tap water at approximately 35-40° C. flowing at about 2 gallons/minute [7570 cc/minute]. Rinse for about 30 seconds and then squeeze out excess water and towel dry with cleaning tissues such as KIMWIPES.

Apply to damaged tresses a strengthening-effective amount of a composition comprising a poly(vinylamine-vinylformamide) copolymer, e.g., LUPAMIN® 9095, and an aqueous carrier. Massage in with fingers and then comb through twice with large teeth and then twice with small teeth of a two-sided comb. Leave in for about 10 minutes and then squeegee out excess solution. Allow the damaged tress to stand for a fixed period of time and then determine tensile strength by testing tress profiles for treated and untreated hair sufficient to measure the F20 Index, while also testing plateau load and break load of the fibers.

It is believed that the composition applied to the damaged tresses will result in improved hair strength by increasing the F20 Index and by increasing the plateau load and break load of the treated fibers.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of strengthening keratinous fibers, the method comprising contacting the fibers with a strengthening-effective amount of a composition consisting of a poly(vinylamine-vinylformamide) copolymer and an aqueous carrier wherein the poly(vinylamine-vinylformamide) copolymer is selected from the group consisting of a high molecular weight poly(vinylamine-vinylformamide) copolymer and a low molecular weight poly(vinylamine-vinylformamide) copolymer.

2. The method of claim 1, wherein the high molecular weight poly(vinylamine-vinylformamide) copolymer comprises at most about 95 mol % vinylamine monomers.

3. The method of claim 1, wherein the high molecular weight poly(vinylamine-vinylformamide) copolymer comprises at most about 50 mol % vinylamine monomers.

4. The method of claim 1, wherein the high molecular weight poly(vinylamine-vinylformamide) copolymer comprises at most about 30 mol % vinylamine monomers.

5. The method of claim 1, wherein the high molecular weight poly(vinylamine-vinylformamide) copolymer comprises at most about 10 mol % vinylamine monomers.

6. The method of claim 1, wherein the low molecular weight poly(vinylamine-vinylformamide) copolymer comprises about 95 mol % vinylamine monomers.

7. The method of claim 1, wherein the composition is in the form of a mousse or a gel.

8. The method of strengthening keratinous fibers according to claim 1, wherein the hair is contacted with the composition for from about 1 minute to about 20 minutes.

\* \* \* \* \*